US008853363B2

(12) United States Patent
Huber et al.

(10) Patent No.: US 8,853,363 B2
(45) Date of Patent: Oct. 7, 2014

(54) SUBSTANCE BINDING HUMAN IGG FC RECEPTOR IIB (FCγRIIB)

(75) Inventors: Robert Huber, München (DE); Peter Sondermann, Rudolfstetten (CH); Uwe Jacob, München (DE); Kerstin Wendt, Brand-Erbisdorf (DE); Chiara Cabrele, Regensburg (DE); Luis Moroder, Martinsried (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 1012 days.

(21) Appl. No.: 10/580,813

(22) PCT Filed: Nov. 26, 2004

(86) PCT No.: PCT/EP2004/013450
§ 371 (c)(1),
(2), (4) Date: Feb. 2, 2007

(87) PCT Pub. No.: WO2005/051999
PCT Pub. Date: Jun. 9, 2005

(65) Prior Publication Data
US 2008/0014141 A1  Jan. 17, 2008

(30) Foreign Application Priority Data
Nov. 26, 2003 (EP) .................................. 03027000

(51) Int. Cl.
C07K 16/00 (2006.01)
C12P 21/08 (2006.01)
C07K 14/735 (2006.01)
C07K 16/28 (2006.01)
C07K 1/00 (2006.01)
A61K 39/00 (2006.01)

(52) U.S. Cl.
CPC ....... C07K 14/70535 (2013.01); *C07K 2317/34* (2013.01); *A61K 2039/505* (2013.01); *C07K 16/283* (2013.01)
USPC ............... 530/387.1; 530/388.1; 530/388.15; 530/388.22; 530/388.73

(58) Field of Classification Search
None
See application file for complete search history.

(56) References Cited

U.S. PATENT DOCUMENTS

| | | | | | |
|---|---|---|---|---|---|
| 5,965,709 | A | * | 10/1999 | Presta et al. | 530/387.3 |
| 7,425,620 | B2 | * | 9/2008 | Koenig et al. | 530/387.1 |
| 2004/0157214 | A1 | * | 8/2004 | McCafferty et al. | 435/5 |
| 2004/0253221 | A1 | | 12/2004 | Arai et al. | |
| 2005/0002924 | A1 | | 1/2005 | Huber et al. | |
| 2005/0287148 | A1 | * | 12/2005 | Chatterjee et al. | 424/155.1 |
| 2008/0214459 | A1 | | 9/2008 | Huber et al. | |

FOREIGN PATENT DOCUMENTS

| | | | |
|---|---|---|---|
| EP | 1 298 205 A1 | | 4/2003 |
| JP | 2002-531086 T | | 9/2002 |
| JP | 2003-199588 | | 7/2003 |
| WO | WO-99/67293 A | | 12/1999 |
| WO | WO 00/05389 | * | 2/2000 |
| WO | WO-00/15214 A | | 3/2000 |
| WO | WO 00/32767 | | 6/2000 |
| WO | WO-00/32767 A | | 6/2000 |
| WO | WO-01/75067 A | | 10/2001 |
| WO | WO 02/27662 A1 | | 1/2002 |
| WO | WO 02/31131 A1 | | 4/2002 |
| WO | WO 03/043648 A2 | | 5/2003 |
| WO | WO-031054213 A | | 7/2003 |

OTHER PUBLICATIONS

MacCallum et al. J. Mol. Biol. (1996) 262, 732-745.*
Pascalis et al. The Journal of Immunology (2002) 169, 3076-3084.*
Casset et al. BBRC(2003) 307, 198-205.*
Vajdos et al. JMB (2002) 320, 415-428.*
Holm et al. Molecular Immunology (2007) 44, 1075-1084).*
Rudikoff et al. PNAS 1982 vol. 79 pp. 1979-1983.*
Rudikoff et al. PNAS 1982 vol. 79, pp. 1979-1983.*
Rader et al. PNAS. 1998. 95:8910-8915.*
Veri et al. Immunology, 2007. 121:392-404.*
Janeway et al., Immunology Third Edition, Garland Publishing Inc. 1997, Chapter 3, Structure of the Antibody Molecule and Immunoglobulin Genes, pp. 3:1-3:11.*
Rudikoff et al. PNAS 1982 vol. 79 p. 1979-1983.*
Fundamental Immunology, William E. Paul, M.D. ed., 3rd ed. 1993, p. 242.*
Portolano et al., Journal of Immunology, 1993 150:880-887.*
Tibbetts, et al. Linear and Cyclic LFA-1 and ICAM-1 Peptides Inhibit T Cell Adhesion and Function, Peptides, (vol. 21, No. 8, pp. 1161-1167) (Elsevier (2000).
Abstract of WO-01/75067—Drmanac, et al. "New Isolated Polynucleotide and encoded polypeptides, useful in diagnostics, forensics, gene mapping, identification of mutations responsible for genetic disorders or other traits and to assess biodiversity", Accession No. ABG-22856 XP-002328367 (Feb. 2002).
Misumi, et al. "A Novel Cyclic Peptide Immunization Strategy for Preventing HIV-1/AIDS Infection and Progression", *J. Biol. Chem.* vol. 278, No. 34 (2003), pp. 32335-32343.
Vidarsson, et al. "Multiplex screening for functionally rearranged immunoglobulin variable regions reveals expression of hybridoma-specific aberrant V-genes", *J. Immunol. Methods* 249 (2001), pp. 245-252.
Pritchard, et al. "B cell inhibitory receptors and autoimmunity", Immunology 108 (2003), pp. 263-273.
Smith, et al. "FcγRIIB in autoimmunity and infection: evolutionary and therapeutic implications" Nature Reviews, Immunology, 328, vol. 10 (2010), pp. 328-343.

(Continued)

*Primary Examiner* — Chun Dahle
(74) *Attorney, Agent, or Firm* — Fulbright & Jaworski LLP

(57) ABSTRACT

The invention relates to novel immunogens carrying conformationally discriminating epitopes (CDEs) and to immunization methods for producing antibodies that specifically recognize proteins with very closely related homologues. In particular, the invention relates to antibodies which are specific for either FcγRIIb or FcγRIIa.

3 Claims, 8 Drawing Sheets

(56) References Cited

OTHER PUBLICATIONS

Figure 2:
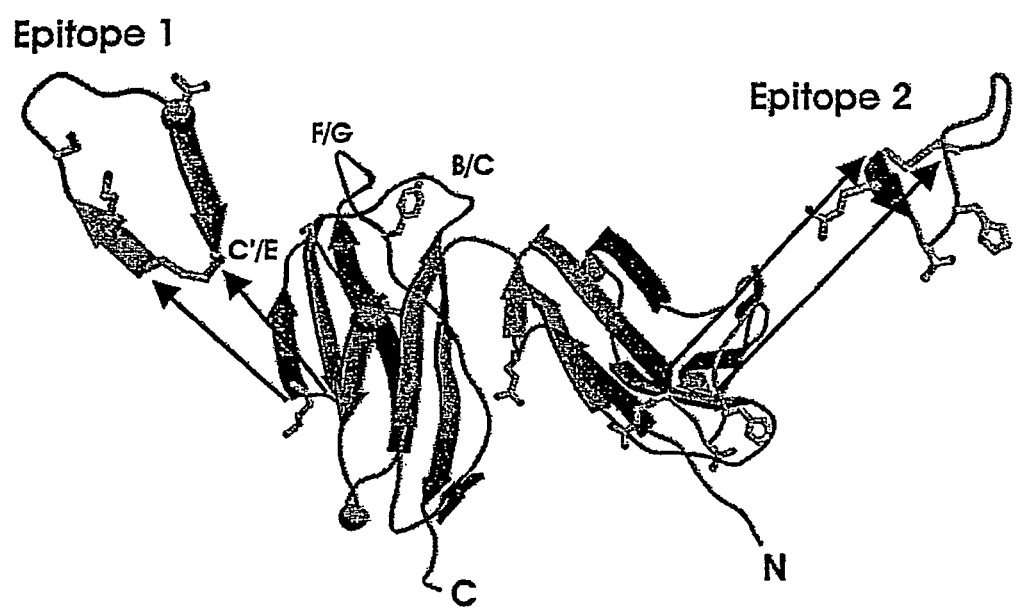

Brauweiler, et al. "FcγRIIB activation leads to inhibition of signalling by independently ligated receptors", Biochem. Soc. (2003), pp. 281-285.

Heymann, Birgitta "Feedback regulation by IgG antibodies", Immunol. Letters, 88 (2003), pp. 157-161.

Jefferis, et al. "IgG-Rc-mediated effector functions: molecular definition of interaction sites for effector ligands and the role of glycosylation", Immunol. Reviews 163 (1998), pp. 59-76.

Lund, et al. "A protein structural change in aglycosylated IgG3 correlates with loss of huFcγR1 and huFcγR111 binding and/or activation", Molecular Immunology 27, No. 11 (1990), pp. 1145-1153.

Sármay, et al. "Integration of activatory and inhibitory signals in human B-cells", Immunol. Letters, 54 (1996), pp. 93-100.

Shields, et al. "High Resolution Mapping of the Binding Site on Human IgG1 for FcγRI, FcγRII, FcγRIII, and FcRn and Design of IgG1 Variants with Improved Binding to the FcγR", J. Biol. Chem., 276, No. 9 (2001), pp. 6591-6604.

Shields, et al. "Lack of Fucose on Human IgG1 N-Linked Oligosaccharide Improves Binding to Human FcγRIII and Antibody-dependent Cellular Toxicity", J. Biol. Chem., 277, No. 30 (2002), pp. 26733-26740.

Shinkawa, et al. "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", J. Biol. Chem., 278, No. 5 (2003), pp. 3466-3473.

Umaña, et al. "Engineered glycoforms of an antineuroblastoma IgG1 with optimized antibody-dependent cellular cytotoxic activity", Nature Biotechnol., 17 (1999), pp. 176-180.

\* cited by examiner

Figure 1:

```
              1         10         20         30         40         50        59
              |         |          |          |          |          |          |
FcγRIIa    AAPPKAVLKLEP P WINVLQEDSVTLTC Q G AR SPESDSIQWFHNGNLIPTHTQPSYRFKAN
FcγRIIb    AAPPKAVLKLEP Q WINVLQEDSVTLTC R G TH SPESDSIQWFHNGNLIPTHTQPSYRFKAN
           ***********  ************** *  *****************************

60        70         80         90        100        110       119
              |         |          |          |          |          |          |
FcγRIIa    NNDSGEYTCQTGQTSLSDPVHLTVLSEWLVLQTPHLEFQEGETI M LRCHSWKDKPLVKVT
FcγRIIb    NNDSGEYTCQTGQTSLSDPVHLTVLSEWLVLQTPHLEFQEGETI V LRCHSWKDKPLVKVT
           ******************************************  **************

120       130        140        150        160        170
              |         |          |          |          |          |
FcγRIIa    FFQNGKS Q KFSR L DP T FSIPQANHSHSGDYHCTGNIGYTL F SSKPVTITVQ V P
FcγRIIb    FFQNGKS K KFSR S DP N FSIPQANHSHSGDYHCTGNIGYTL Y SSKPVTITVQ A P
           *******  ****  **  ************************  ********** *
```

Figure 5:

a) Variable light region of mAb GB3

```
agaattcagctgacccagtctccatcctccttatctgcctctctgggagaaagagtcagt
 R  I  Q  L  T  Q  S  P  S  S  L  S  A  S  L  G  E  R  V  S ctcacttgtcgggcaagtcaggaaattagtggttacttaagctggcttcagcagaaacca
 L  T  C  R  A  S  Q  E  I  S  G  Y  L  S  W  L  Q  Q  K  P
           CDR1 gatggaactattaaacgcctgatctacgccacatccgctttagattctggtgtcccaaaa
 D  G  T  I  K  R  L  I  Y  A  T  S  A  L  D  S  G  V  P  K
                         CDR2 aggttcagtggcagtgggtctgggtcaaattattctctcaccatcagcagccttgagtct
 R  F  S  G  S  G  S  G  S  N  Y  S  L  T  I  S  S  L  E  S gaagattttgcagactattactgtctacaatatgctaattatccgtacacgttcgagggg
 E  D  F  A  D  Y  Y  C  L  Q  Y  A  N  Y  P  Y  T  F  G  G
                         CDR3 gggaccaagctg
 G  T  K  L
``` b) Variable heavy region of mAb GB3

```
gtgcagctgcagcagtctggacctgagctggtgaagcctggggcttcagtgaagatttcc
 V  Q  L  Q  Q  S  G  P  E  L  V  K  P  G  A  S  V  K  I  S tgcaaggcttctggctacaccttcactgactactatatactgggtgaaacagtggcct
 C  K  A  S  G  Y  T  F  T  D  Y  Y  I  Y  W  V  K  Q  W  P
           CDR1 ggacagggacttgagtggattggatggattttcctggaactggtaatacttactacaat
 G  Q  G  L  E  W  I  G  W  I  F  P  G  T  N  T  Y  Y  N
                      CDR2 gaaaacttcaaggacaaggccacacttactatagatagatcctccagcacagcctacatg
 E  N  F  K  D  K  A  T  L  T  I  D  R  S  S  S  T  A  Y  M
    CDR2 (contd.)

ttgctcggcagcctgacctctgaggactctgcggtctatttctgttatggtccgtttgct
 L  L  G  S  L  T  S  E  D  S  A  V  Y  F  C  Y  G  P  F  A
                                              CDR3 tactgggggccaa
 Y  W  G  Q
CDR3
```

Figure 6:

Variable heavy region of mAb CE5:

<u>tgcaggagtcaggacctggcctggt</u>ggcgccctcacagagcctgtccatcacatgcaccgtct
L  Q  E  S  G  P  G  L  V  A  P  S  Q  S  L  S  I  T  C  T  V cagggttctcatt<u>aaccggctatggtgtaaac</u>tgggttcgccagcctccaggaaagggtctgg
S  |G  F  S  L  T  G  Y  G  V  N|  W  V  R  Q  P  P  G  K  G  L
        CDR1 agtggctgggaa<u>tgatttggggtgatggaaacacagactataattcagctctcaaatccagac</u>
E  W  L  G  |M  I  W  G  D  G  N  T  D  Y  N  S  A  L  K  S|  R
                                      CDR2 tgagcatcagcaaggacaactccaagagccaagttttcttaaaaatgaacagtctgcacactg
L  S  I  S  K  D  N  S  K  S  Q  V  F  L  K  M  N  S  L  H  T atgacacagccaggtactactgtgccagagagagagattataggcttgactact<u>gggggcaag</u>
D  D  T  A  R  Y  Y  C  A  R  |E  R  D  Y  R  L  D  Y|  W  G  Q
                                  CDR3

<u>ggaccacggtcaccgtctcctcag</u>
G  T  T  V  T  V  S  S

Variable light region of mAb CE5:

<u>gagctcacccagtctccagcctcccttttct</u>gcgtctgtgggagaaactgtcaccatcacatgt
E  L  T  Q  S  P  A  S  L  S  A  S  V  G  E  T  V  T  I  T  C <u>cgagcaagtgggaatattcacaattatttag</u>catggtatcagcagaaacagggaaaatctcct
|R  A  S  G  N  I  H  N  Y  L  A|  W  Y  Q  Q  K  Q  G  K  S  P
        CDR1 cagctcctggtctat<u>tatacaacaaccttagcagat</u>ggtgtgccatcaaggttcagtggcagt
Q  L  L  V  Y  |Y  T  T  T  L  A  D|  G  V  P  S  R  F  S  G  S
                      CDR2 ggatcaggaacacaatattctctcaagatcaacagcctgcaacctgaagatttggggagttat
G  S  G  T  Q  Y  S  L  K  I  N  S  L  Q  P  E  D  F  G  S  Y tactgt<u>caacattttggagtactcctcggacgttcggtggaggga</u>ccaagctcgag
Y  C  |Q  H  F  W  S  T  P  R  T|  F  G  G  G  T  K  L  E
        CDR3

SEQUENCE LISTING

```
<160> NUMBER OF SEQ ID NOS: 11

<210> SEQ ID NO 1
<211> LENGTH: 172
<212> TYPE: PRT
<213> ORGANISM: human
<220> FEATURE:
<223> OTHER INFORMATION: Fc gamma RIIa

<400> SEQUENCE: 1

Ala Pro Pro Lys Ala Val Leu Lys Leu Glu Pro Pro Trp Ile Asn Val
 1               5                  10                  15

Leu Gln Glu Asp Ser Val Thr Leu Thr Cys Gln Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

Lys Pro Leu Val Lys Val Thr Phe Phe Gln Asn Gly Lys Ser Gln Lys
        115                 120                 125

Phe Ser Arg Leu Asp Pro Thr Phe Ser Ile Pro Gln Ala Asn His Ser
    130                 135                 140

His Ser Gly Asp Tyr His Cys Thr Gly Asn Ile Gly Tyr Thr Leu Phe
145                 150                 155                 160

Ser Ser Lys Pro Val Thr Ile Thr Val Gln Val Pro
                165                 170

<210> SEQ ID NO 2
```

```
<211> LENGTH: 172
<212> TYPE: PRT
<213> ORGANISM: human
<220> FEATURE:
<223> OTHER INFORMATION: Fc gamma RIIb

<400> SEQUENCE: 2

Ala Pro Pro Lys Ala Val Leu Lys Leu Glu Pro Gln Trp Ile Asn Val
 1               5                  10                  15

Leu Gln Glu Asp Ser Val Thr Leu Thr Cys Arg Gly Thr His Ser Pro
                20                  25                  30

Glu Ser Asp Ser Ile Gln Trp Phe His Asn Gly Asn Leu Ile Pro Thr
            35                  40                  45

His Thr Gln Pro Ser Tyr Arg Phe Lys Ala Asn Asn Asn Asp Ser Gly
        50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Lys Lys
        115                 120                 125

Phe Ser Arg Ser Asp Pro Asn Phe Ser Ile Pro Gln Ala Asn His Ser
    130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln Ala Pro
                165                 170

<210> SEQ ID NO 3
<211> LENGTH: 13
<212> TYPE: PRT
<213> ORGANISM: human
<220> FEATURE:
<223> OTHER INFORMATION: glycopeptide CDE [126-137]

<400> SEQUENCE: 3

Ser Lys Lys Phe Ser Arg Ser Asp Pro Asn Phe Ser Gly
 1               5                  10

<210> SEQ ID NO 4
<211> LENGTH: 312
<212> TYPE: DNA
<213> ORGANISM: Unknown Organism
<220> FEATURE:
<221> NAME/KEY: CDS
<222> LOCATION: (1)..(312)
<223> OTHER INFORMATION: variable light region of mAb GB3
<220> FEATURE:
<223> OTHER INFORMATION: Description of Unknown Organism: sequence
      comprised by an antibody

<400> SEQUENCE: 4 aga att cag ctg acc cag tct cca tcc tcc tta tct gcc tct ctg gga     48
Arg Ile Gln Leu Thr Gln Ser Pro Ser Ser Leu Ser Ala Ser Leu Gly
 1               5                  10                  15 gaa aga gtc agt ctc act tgt cgg gca agt cag gaa att agt ggt tac     96
Glu Arg Val Ser Leu Thr Cys Arg Ala Ser Gln Glu Ile Ser Gly Tyr
                20                  25                  30 tta agc tgg ctt cag cag aaa cca gat gga act att aaa cgc ctg atc    144
Leu Ser Trp Leu Gln Gln Lys Pro Asp Gly Thr Ile Lys Arg Leu Ile
```

```
                35                  40                  45
tac gcc aca tcc gct tta gat tct ggt gtc cca aaa agg ttc agt ggc      192
Tyr Ala Thr Ser Ala Leu Asp Ser Gly Val Pro Lys Arg Phe Ser Gly
         50                  55                  60 agt ggg tct ggg tca aat tat tct ctc acc atc agc agc ctt gag tct      240
Ser Gly Ser Gly Ser Asn Tyr Ser Leu Thr Ile Ser Ser Leu Glu Ser
 65                  70                  75                  80 gaa gat ttt gca gac tat tac tgt cta caa tat gct aat tat ccg tac      288
Glu Asp Phe Ala Asp Tyr Tyr Cys Leu Gln Tyr Ala Asn Tyr Pro Tyr
                 85                  90                  95 acg ttc gga ggg ggg acc aag ctg                                      312
Thr Phe Gly Gly Gly Thr Lys Leu
            100

<210> SEQ ID NO 5
<211> LENGTH: 104
<212> TYPE: PRT
<213> ORGANISM: Unknown Organism
<220> FEATURE:
<223> OTHER INFORMATION: Description of Unknown Organism: sequence
      comprised by an antibody

<400> SEQUENCE: 5

Arg Ile Gln Leu Thr Gln Ser Pro Ser Ser Leu Ser Ala Ser Leu Gly
  1               5                  10                  15

Glu Arg Val Ser Leu Thr Cys Arg Ala Ser Gln Glu Ile Ser Gly Tyr
             20                  25                  30

Leu Ser Trp Leu Gln Gln Lys Pro Asp Gly Thr Ile Lys Arg Leu Ile
         35                  40                  45

Tyr Ala Thr Ser Ala Leu Asp Ser Gly Val Pro Lys Arg Phe Ser Gly
     50                  55                  60

Ser Gly Ser Gly Ser Asn Tyr Ser Leu Thr Ile Ser Ser Leu Glu Ser
 65                  70                  75                  80

Glu Asp Phe Ala Asp Tyr Tyr Cys Leu Gln Tyr Ala Asn Tyr Pro Tyr
                 85                  90                  95

Thr Phe Gly Gly Gly Thr Lys Leu
            100

<210> SEQ ID NO 6
<211> LENGTH: 312
<212> TYPE: DNA
<213> ORGANISM: Unknown Organism
<220> FEATURE:
<221> NAME/KEY: CDS
<222> LOCATION: (1)..(312)
<223> OTHER INFORMATION: variable heavy region of mAb GB3
<220> FEATURE:
<223> OTHER INFORMATION: Description of Unknown Organism: sequence
      comprised by an antibody

<400> SEQUENCE: 6 gtg cag ctg cag cag tct gga cct gag ctg gtg aag cct ggg gct tca       48
Val Gln Leu Gln Gln Ser Gly Pro Glu Leu Val Lys Pro Gly Ala Ser
  1               5                  10                  15 gtg aag att tcc tgc aag gct tct ggc tac acc ttc act gac tac tat       96
Val Lys Ile Ser Cys Lys Ala Ser Gly Tyr Thr Phe Thr Asp Tyr Tyr
             20                  25                  30 ata tac tgg gtg aaa cag tgg cct gga cag gga ctt gag tgg att gga      144
Ile Tyr Trp Val Lys Gln Trp Pro Gly Gln Gly Leu Glu Trp Ile Gly
         35                  40                  45 tgg att ttt cct gga act ggt aat act tac tac aat gaa aac ttc aag      192
Trp Ile Phe Pro Gly Thr Gly Asn Thr Tyr Tyr Asn Glu Asn Phe Lys
```

```
                          50                  55                  60
gac aag gcc aca ctt act ata gat aga tcc tcc agc aca gcc tac atg        240
Asp Lys Ala Thr Leu Thr Ile Asp Arg Ser Ser Thr Ala Tyr Met
 65                  70                  75                  80 ttg ctc ggc agc ctg acc tct gag gac tct gcg gtc tat ttc tgt tat        288
Leu Leu Gly Ser Leu Thr Ser Glu Asp Ser Ala Val Tyr Phe Cys Tyr
                 85                  90                  95 ggt ccg ttt gct tac tgg ggc caa                                        312
Gly Pro Phe Ala Tyr Trp Gly Gln
                100
```

<210> SEQ ID NO 7
<211> LENGTH: 104
<212> TYPE: PRT
<213> ORGANISM: Unknown Organism
<220> FEATURE:
<223> OTHER INFORMATION: Description of Unknown Organism: sequence
      comprised by an antibody

<400> SEQUENCE: 7

```
Val Gln Leu Gln Gln Ser Gly Pro Glu Leu Val Lys Pro Gly Ala Ser
 1               5                  10                  15

Val Lys Ile Ser Cys Lys Ala Ser Gly Tyr Thr Phe Thr Asp Tyr Tyr
                20                  25                  30

Ile Tyr Trp Val Lys Gln Trp Pro Gly Gln Gly Leu Glu Trp Ile Gly
            35                  40                  45

Trp Ile Phe Pro Gly Thr Gly Asn Thr Tyr Tyr Asn Glu Asn Phe Lys
        50                  55                  60

Asp Lys Ala Thr Leu Thr Ile Asp Arg Ser Ser Thr Ala Tyr Met
 65                  70                  75                  80

Leu Leu Gly Ser Leu Thr Ser Glu Asp Ser Ala Val Tyr Phe Cys Tyr
                85                  90                  95

Gly Pro Phe Ala Tyr Trp Gly Gln
                100
```

<210> SEQ ID NO 8
<211> LENGTH: 309
<212> TYPE: DNA
<213> ORGANISM: Unknown Organism
<220> FEATURE:
<221> NAME/KEY: CDS
<222> LOCATION: (1)..(309)
<223> OTHER INFORMATION: variable light region of mAb CE5
<220> FEATURE:
<223> OTHER INFORMATION: Description of Unknown Organism: sequence
      comprised by an antibody

<400> SEQUENCE: 8

```
gag ctc acc cag tct cca gcc tcc ctt tct gcg tct gtg gga gaa act         48
Glu Leu Thr Gln Ser Pro Ala Ser Leu Ser Ala Ser Val Gly Glu Thr
 1               5                  10                  15 gtc acc atc aca tgt cga gca agt ggg aat att cac aat tat tta gca         96
Val Thr Ile Thr Cys Arg Ala Ser Gly Asn Ile His Asn Tyr Leu Ala
                20                  25                  30 tgg tat cag cag aaa cag gga aaa tct cct cag ctc ctg gtc tat tat        144
Trp Tyr Gln Gln Lys Gln Gly Lys Ser Pro Gln Leu Leu Val Tyr Tyr
            35                  40                  45 aca aca acc tta gca gat ggt gtg cca tca agg ttc agt ggc agt gga        192
Thr Thr Thr Leu Ala Asp Gly Val Pro Ser Arg Phe Ser Gly Ser Gly
        50                  55                  60 tca gga aca caa tat tct ctc aag atc aac agc ctg caa cct gaa gat        240
Ser Gly Thr Gln Tyr Ser Leu Lys Ile Asn Ser Leu Gln Pro Glu Asp
```

```
                65                  70                  75                  80
ttt ggg agt tat tac tgt caa cat ttt tgg agt act cct cgg acg ttc      288
Phe Gly Ser Tyr Tyr Cys Gln His Phe Trp Ser Thr Pro Arg Thr Phe
                85                  90                  95 ggt gga ggg acc aag ctc gag                                          309
Gly Gly Gly Thr Lys Leu Glu
        100

<210> SEQ ID NO 9
<211> LENGTH: 103
<212> TYPE: PRT
<213> ORGANISM: Unknown Organism
<220> FEATURE:
<223> OTHER INFORMATION: Description of Unknown Organism: sequence
      comprised by an antibody

<400> SEQUENCE: 9

Glu Leu Thr Gln Ser Pro Ala Ser Leu Ser Ala Ser Val Gly Glu Thr
 1               5                  10                  15

Val Thr Ile Thr Cys Arg Ala Ser Gly Asn Ile His Asn Tyr Leu Ala
                20                  25                  30

Trp Tyr Gln Gln Lys Gln Gly Lys Ser Pro Gln Leu Leu Val Tyr Tyr
            35                  40                  45

Thr Thr Thr Leu Ala Asp Gly Val Pro Ser Arg Phe Ser Gly Ser Gly
        50                  55                  60

Ser Gly Thr Gln Tyr Ser Leu Lys Ile Asn Ser Leu Gln Pro Glu Asp
 65                  70                  75                  80

Phe Gly Ser Tyr Tyr Cys Gln His Phe Trp Ser Thr Pro Arg Thr Phe
                85                  90                  95

Gly Gly Gly Thr Lys Leu Glu
        100

<210> SEQ ID NO 10
<211> LENGTH: 339
<212> TYPE: DNA
<213> ORGANISM: Unknown Organism
<220> FEATURE:
<221> NAME/KEY: CDS
<222> LOCATION: (3)..(338)
<223> OTHER INFORMATION: variable heavy region of mAb CE5
<220> FEATURE:
<223> OTHER INFORMATION: Description of Unknown Organism: sequence
      comprised by an antibody

<400> SEQUENCE: 10 tg cag gag tca gga cct ggc ctg gtg gcg ccc tca cag agc ctg tcc       47
   Gln Glu Ser Gly Pro Gly Leu Val Ala Pro Ser Gln Ser Leu Ser
    1               5                  10                  15 atc aca tgc acc gtc tca ggg ttc tca tta acc ggc tat ggt gta aac      95
Ile Thr Cys Thr Val Ser Gly Phe Ser Leu Thr Gly Tyr Gly Val Asn
                20                  25                  30 tgg gtt cgc cag cct cca gga aag ggt ctg gag tgg ctg gga atg att     143
Trp Val Arg Gln Pro Pro Gly Lys Gly Leu Glu Trp Leu Gly Met Ile
            35                  40                  45 tgg ggt gat gga aac aca gac tat aat tca gct ctc aaa tcc aga ctg     191
Trp Gly Asp Gly Asn Thr Asp Tyr Asn Ser Ala Leu Lys Ser Arg Leu
        50                  55                  60 agc atc agc aag gac aac tcc aag agc caa gtt ttc tta aaa atg aac     239
Ser Ile Ser Lys Asp Asn Ser Lys Ser Gln Val Phe Leu Lys Met Asn
 65                  70                  75 agt ctg cac act gat gac aca gcc agg tac tac tgt gcc aga gag aga     287
Ser Leu His Thr Asp Asp Thr Ala Arg Tyr Tyr Cys Ala Arg Glu Arg
```

```
                80                   85                    90                   95
gat tat agg ctt gac tac tgg ggc caa ggg acc acg gtc acc gtc tcc      335
Asp Tyr Arg Leu Asp Tyr Trp Gly Gln Gly Thr Thr Val Thr Val Ser
                    100                  105                  110 tca g                                                                339
Ser

<210> SEQ ID NO 11
<211> LENGTH: 112
<212> TYPE: PRT
<213> ORGANISM: Unknown Organism
<220> FEATURE:
<223> OTHER INFORMATION: Description of Unknown Organism: sequence
      comprised by an antibody

<400> SEQUENCE: 11

Gln Glu Ser Gly Pro Gly Leu Val Ala Pro Ser Gln Ser Leu Ser Ile
 1               5                  10                  15

Thr Cys Thr Val Ser Gly Phe Ser Leu Thr Gly Tyr Gly Val Asn Trp
            20                  25                  30

Val Arg Gln Pro Pro Gly Lys Gly Leu Glu Trp Leu Gly Met Ile Trp
        35                  40                  45

Gly Asp Gly Asn Thr Asp Tyr Asn Ser Ala Leu Lys Ser Arg Leu Ser
    50                  55                  60

Ile Ser Lys Asp Asn Ser Lys Ser Gln Val Phe Leu Lys Met Asn Ser
65                  70                  75                  80

Leu His Thr Asp Asp Thr Ala Arg Tyr Tyr Cys Ala Arg Glu Arg Asp
                85                  90                  95

Tyr Arg Leu Asp Tyr Trp Gly Gln Gly Thr Thr Val Thr Val Ser Ser
            100                 105                 110
```

SUBSTANCE BINDING HUMAN IGG FC RECEPTOR IIB (FCγRIIB)

This is a §371 of PCT/EP2004/013450 filed Nov. 26, 2004, which claims priority from European Patent Application No. 03 027 000.3 filed Nov. 26, 2003.

The invention relates to novel immunogens carrying conformationally discriminating epitopes (CDEs) and to immunization methods for producing antibodies that specifically recognize proteins with very closely related homologues. In particular, the invention relates to antibodies which are specific for either FcγRIIb or FcγRIIa and which are useful for the diagnosis and treatment of autoimmune diseases, infections, tumors and other conditions where the immune system is involved.

Fc receptors (FcRs) play a key role in defending the human organism against infections. After pathogens have gained access to the blood circulation they are opsonized by antibodies (immunoglobulins, Igs). This leads to the formation of immune complexes. The Fc portions of the antibodies can bind to Fc receptors which are present on virtually all cells of the immune system. Specific FcRs exist for all Ig classes. The Greek letter indicates the Ig class to which it binds, i.e. Fcγ receptors recognize IgG etc.

It has been known for a number of years that the Fc receptors for IgG (FcγR) play an important role in triggering effector responses (Metzger, 1992A). These include, depending on the expressed FcγR and cell type, endo- and phagocytosis resulting in neutralization of the pathogens and antigen presentation, antibody-dependent cell-mediated cytotoxicity (ADCC), neutrophil activation, regulation of the antibody production or the secretion of inflammatory mediators (Fridman et al., 1992; van de Winkel and Capel, 1993; Ravetch and Bolland, 2001).

In contrast to the beneficial role FcRs play in the healthy individual, they also transmit the stimulation of the immune system in allergies (e.g. mediated by FcεRIa) or autoimmune diseases. Moreover, some viruses employ FcγRs to get access to cells like HIV (Homsy et al., 1989) and Dengue (Littaua et al., 1990) or slow down the immune response by blocking FcγRs as in the case of Ebola (Yang et al., 1998) and Measles (Ravanel et al., 1997).

Fc receptors for IgG (FcγR) are the most widespread of the Fc receptor family and are expressed in a defined pattern on all immunological active cells. FcγRI is constitutively expressed on monocytes and macrophages and can be induced on neutrophils and eosinophils. The physiological role of FcγRI is still unknown as the expression on monocytes is not vital (Ceuppens et al., 1988). The glycosylphosphatidylinositol-anchored form (GPI) of FcγRIII (FcγRIIIb) is exclusively expressed on granulocytes. Due to its missing cytoplasmic part, the signal transduction into the cell occurs solely via other transmembrane proteins like complement receptor type 3 (CR3) that can at least associate with FcγRIIIb (Zhou et al., 1993; Poo et al., 1995). FcγRIIIa is mainly expressed on monocytes and macrophages but only in conjunction with an associated protein called γ-chain. FcγRIIa is the receptor with the widest distribution on immune competent cells and is mainly involved in the endocytosis of immune complexes. FcγRIIb is expressed on B cells where it is the only IgG receptor, and on effector cells such as macrophages, neutrophils and mast cells, but not on NK cells and T cells.

Structurally, the extracellular part of the FcγRs consists of three (FcγRI, CD64) or two (FcεRI, FcγRII, CD32 and FcγRIII, CD16) Ig-like domains (ca. 10 kDa/domain) and therefore belong to the immunoglobulin super family. In addition to the extracellular domains, FcRs have a transmembrane domain, and an intracellular domain with the exception of the GPI-anchored FcγRIIIb. The receptors are homologous to each other, and the overall identity in amino acid sequence among the FcγRs and the FcεRIa exceeds 40% in their extracellular regions. FcγRIIa and FcγRIIb differ in their extracellular region by only 6% of the amino acid residues. Nevertheless, both forms can be distinguished by their binding characteristics to human and mouse IgG subclasses (van de Winkel and Capel, 1993) and their differing affinity to human IgGs (Sondermann et al., 1999A).

FcRs are highly glycosylated. The cDNA sequence of many Fc receptors is known, and some soluble recombinant FcR have been generated. Soluble recombinant Fc receptors which are characterised by an absence of transmembrane domains, signal peptide and glycosylation are disclosed in WO 00/32767.

FcγRs occur in various isoforms (FcγRIa, b1, b2, c; FcγRIIa1-2, b1-3, c) and alleles (FcγRIIa1-HR, -LR; FcγRIIIb-NA1, -NA2) (van de Winkel and Capel, 1993). In contrast to the overall homologous extracellular parts, the membrane spanning and the cytoplasmic domains of up to 8 kDa large differ.

The FcγRs can be divided into two general classes according to their function which may be an activating or an inhibitory one. The activating receptors are associated with a cytoplasmic 16 amino acid immunoreceptor tyrosine-based activation motif (ITAM) having the consensus sequence $Y-X_2-L/I-X-Y-X_2-L/I$ (Isakov, 1997). This motif can be found, for example in FcγRIIa. The other class of FcRs are inhibitory receptors which have a cytoplasmic 6 amino acid inhibitory motif (ITIM) having the consensus sequence $V/I-X-Y-X_2-V/L$ (Isakov, 1997). An example of such an inhibitory FcR is FcγRIIb.

Activation and inhibition via the ITAM and ITIM motifs is effected by tyrosine phosphorylation. Depending on the particular cell type, activated by the Fc receptor, different tyrosine kinases are involved in these signaling pathways (Amigorena et al., 1992). Both activating and inhibiting FcγRs may be expressed on the same cell which allows functioning of activation and inhibitory receptors in concert for a fine tuning of the immune response.

FcγRIIb has two inhibitory activities. One of these is dependent on the ITIM motif and occurs when FcγRIIb is ligated to an ITAM-carrying receptor (e.g. FcγRIIa) resulting in the inhibition of ITAM-triggered calcium mobilization and cellular proliferation. This means that calcium-dependent processes such as degranulation, phagocytosis, ADCC, cytokine release and pro-inflammatory activation, and also B cell proliferation are blocked by FcγRIIb. The second inhibitory activity of FcγRIIb involves homo-aggregation of the receptor (FcγRIIb clustering) which delivers a pro-apoptotic signal into the cytoplasm. The pro-apoptotic signal has only been reported in B cells and can be blocked by ligation of FcγRIIb to the B cell receptor (BCR). In vivo studies suggest that FcγRIIb plays a role in peripheral tolerance because FcγRIIb-knockout mice develop spontaneously autoimmune diseases. On the other hand, FcγRIIb has also been reported to down-regulate cytotoxicity is against tumors (Clynes et al., 2000). Mice deficient in FcγRIIb and treated with an anti-tumor antibody showed enhanced ADCC resulting in a reduction of tumor metastasis, whereas mice deficient in activating Fc receptors were unable to arrest tumor growth, when treated with the same antibody.

The generation of antibodies by immunising animals with proteins or peptides as immunogens is known in the art. Conventional immunisation protocols use linear peptides as immunogens which are derived from antigens of interest. The disadvantage of such methods is that because the three-dimensional structure of the epitopes is often completely lost, the resulting antibodies are not very specific or they comprise a large fraction of antibodies directed to epitopes other than the one of interest.

During the last decade, immunization protocols using Fc-receptor expressing cells or denatured Fc-receptors have only resulted in antibodies that were able to specifically detect denatured Fc-Receptors (Western Blot) or were not able to discriminate between the related FcγRIIa and FcγRIIb on cell lines (e.g. U-937, Raji) or blood cells. To date, there are no antibodies or other binding substances which bind selectively and specifically to FcγRIIb in its native conformation and/or its natural environment.

Conventional immunization protocols involving peptides or recombinant proteins as antigens are not well suited to produce specific antibodies against proteins for which homologues with very high sequence identity exist. In general, antibodies are raised using small linear peptides as immunogens. Such peptides do not represent the native conformation of the epitope on the protein from which they are derived. In addition, the large majority of the antibodies produced by the immunized animal are directed against epitopes of the carrier protein to which the antigen is conjugated or against epitopes on the recombinant antigen that are common to the homologues. In consequence, the produced antibodies are not specific and/or fail to detect the antigen in its native conformation. Furthermore, glycosylation sites might be located within the epitopes of interest and mask these sites. Conventional immunization protocols which use these epitopes without the respective native glycosylation found in the target molecule result in antibodies that fail to recognize the antigen in its native conformation.

One object of the present invention is to provide recombinant peptides or polypeptides which can be used as immunogens to raise antibodies capable of discriminating between an antigen of interest and closely related antigens, and a method of generating such peptides and the corresponding antibodies and other substances having immunological specificity.

It is a further object of the present invention to provide substances which can selectively bind to and discriminate between Fc receptor subtypes, thereby acting as an Fc receptor binding substance useful for the treatment and diagnosis of immune disorders, in particular autoimmune diseases, and as anti-tumor agents which enhance the efficiency of such therapies by promoting ADCC against tumor cells.

It is a further object of the present invention to provide an immunization protocol that will allow the generation of such FcγRIIb-binding substances, in particular antibodies, especially monoclonal antibodies with the above-mentioned specificity.

The inventors of the present invention have found a novel and inventive approach to developing substances, in particular antibodies, that are capable of discriminating between very closely related proteins and/or proteins and antigens with high homology.

Surprisingly, it was found that it is possible to raise specific antibodies against proteins of interest when so-called conformationally discriminating epitopes (CDEs) are used as the antigen to which the antibodies are raised.

The present invention therefore relates to an artificial peptide or polypeptide comprising a conformationally discriminating epitope (CDE) in its native conformation, wherein the CDE is structurally stabilized by circularization.

For the purposes of the present invention, an artificial peptide or polypeptide is one that is produced by any technical process such as recombinant techniques or preferably by peptide synthesis.

A CDE is an epitope in a protein which has a specific conformation in the protein. Antibodies which are specific for such an epitope can discriminate between a protein and very closely related homologues. The CDE comprises at least one amino acid which differs between the protein in which it is present and the homologues of that protein (unique residue). The unique residues need not be in close proximity in the linear sequence of the protein in order to be part of the same epitope. The advantage of the present invention is that the peptides of the invention do not just have the linear sequence of those epitopes but mimic also their structure. The CDE contains at least one of such unique residues, preferably at least two, more preferably more than two of such unique residues. The CDE represents the binding site for an antibody.

The peptides of the present invention preferably have a length of from 5, more preferably from about 8, more preferably from about 10 to about 30, more preferably to about 20, more preferably to about 18, more preferably to about 15 amino acids.

Structural stabilization in this context means that the peptide is stabilized so that the CDE is present in as close to its native three-dimensional conformation in the original protein as possible. Structural stabilization can be achieved by a number of means. In particular, the peptide is circularized so that it forms a stable three-dimensional structure such as a loop. Stabilizing the peptide can be achieved by N- to C-terminal coupling, the formation of cysteine bridges or by bridging amino acid side chains. Pseudopeptides can be formed.

Preferably, the peptide or polypeptide of the present invention also carries glycosylation moieties. The peptide is preferably generated so that glycosylated amino acids are incorporated at the same sites which are glycosylated in the native protein from which the CDE is derived. Preferably, the glycosylated amino acids are selected from N-acetyl-glucosamine, fucose, xylose, mannose, and galactose conjugates but this list is not exhaustive. If the discriminating epitope contains a N-glycosylation site, an artificial conjugate of an asparagine residue with a N-acetyl-glucosamine may be incorporated into the peptide, to enhance the probability that the natively glycosylated substrate is recognized by the resulting antibodies after successful immunization. Accordingly for O-glycosylation sites, a serine or threonine residue may be conjugated with a mannose, fucose, xylose, galactose or N-Acetyl-galactosamine residue respectively.

The peptides and polypeptides of the invention may additionally be coupled to a carrier molecule. Such carrier molecules are preferably selected from haptens, peptides, polypeptides and other immunogens. The peptides of the invention may be grafted onto other peptides and proteins, even the same protein or parts thereof from which the CDE was derived.

A preferred embodiment of the invention is a peptide carrying a CDE from an Fc receptor. The inventors of the present invention surprisingly found that there are specific epitopes on the extracellular portion of FcγRIIb which allow the generation of antibodies which bind specifically to FcγRIIb. This is particularly useful because the family of Fc receptors comprises unusually closely related homologues which are difficult to distinguish using conventional antibodies. In particular, the present invention makes it possible to generate substances which bind to FcγRIIb but not to FcγRIIa and vice versa. Similarly, the epitopes can be chosen so that FcγRIIa is specifically recognized.

In particular, the peptides or polypeptides according to the present invention comprise an epitope comprising at least one, preferably at least 2, preferably at least 3 of the following amino acids of the amino acid sequence of human FcγRIIb according to FIG. 1 and SEQ ID NO: 2: Gln12, Arg27, Thr29, His30, Val104, Lys127, Ser132, Asn135, Tyr160, and Ala171, or the corresponding amino acids of FcγRIIa according to SEQ ID NO: 1. More preferably, the epitopes useful for the purposes of the present invention comprise amino acids 27 to 30, and/or 127 to 135, and/or 160 to 171 of the amino acid sequence of FcγRIIb (FIG. 1, SEQ. ID NO: 2), or the corresponding amino acids of FcγRIIa (FIG. 1). These peptides can represent FcγRIIb-specific conformationally discriminating epitopes (CDEs), when structurally stabilized by circularization, in an adequate way as exemplified in FIG. 2. Also, the corresponding epitopes of FcγRIIa may be used to produce antibodies that specifically bind only to FcγRIIa.

Especially peptides comprising the amino acid sequence 127-KKFSRSDPN-135 and flanking amino acids are preferred because these peptides represent a FcγRIIb-specific conformational epitope within the binding region of the Fc-Receptor to the Fc-fragment (WO 00/32767, Sondermann et al., 2000; Sondermann et al., 2001). Furthermore peptides containing the amino acid sequence 28-RGTH-31 and flanking residues are preferred because they represent a binding epitope apart from the binding region to the Fc-fragment. Moreover, this epitope may be further adapted to the native structure by circularisation and incorporation of a glycosylated asparagine residue at position 135.

Figure 7:
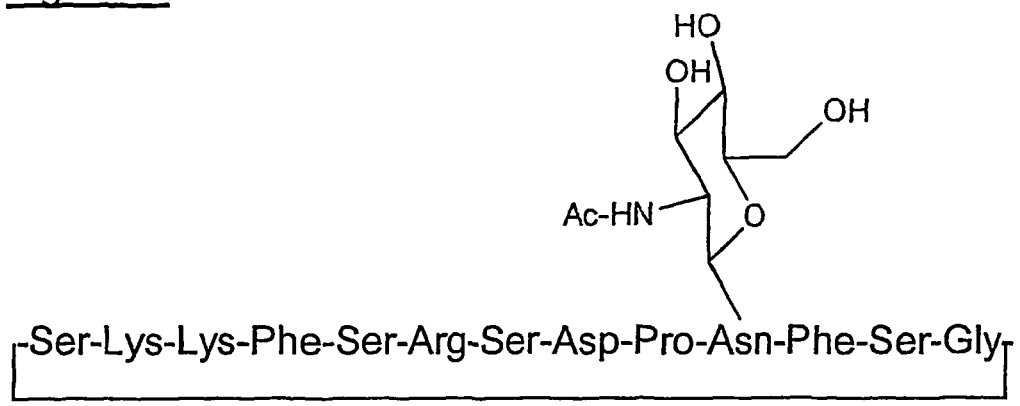

Thus, a preferred embodiment of the present invention is a peptide or polypeptide carrying the CDE according SEQ ID NO: 3. Preferably, the asparagine of position 135 (according to SEQ ID NO: 2) is glycosylated with N-acetyl-glucosamine. Preferably, the peptide is as shown in FIG. 7, being circularized by linking the first and last amino acids in the sequence as shown in FIG. 7.

These artificial peptides can then be used directly for the immunization of animals or may be coupled to a carrier protein such as haptens or peptides or polypeptides, or ideally to the target protein itself. In a preferred embodiment, a CDE from FcγRIIb or FcγRIIa or a peptide carrying such a CDE is conjugated to FcγRIIb or FcγRIIa.

The peptides and polypeptides of the present invention are preferably used as immunogens to immunize animals in order to generate specific antibodies and, with the aid of the sequence of those specific antibodies, further immunologically specific substances. The CDEs and the peptides carrying them may be used for the generation of immunomodulatory substances specifically recognizing the CDE. This is particularly preferred when CDEs of Fc receptors are chosen because they allow the generation of antibodies specific for individual members of the family of homologues. In particular, antibodies and other immunomodulatory substance recognizing either FcγRIIb or FcγRIIa but not both at the same time, can be generated. The present invention allows the generation of antibodies which are capable not only of specifically recognizing FcγRIIb or FcγRIIa and discriminating between the two Fc receptors but also of doing so when the Fc receptors are in their natural environment, for example in cell culture or in vivo, e.g. in the blood stream.

By coupling of the CDE to the protein from which it was derived, the background immune reaction against the carrier protein is reduced. The artificial modification by the covalently coupled CDE results in an increased immune response. This is especially important if the immunized animal expresses similar proteins which would be tolerated by its immune system. Thus, if the peptide of the invention carries a CDE of FcγRIIb or FcγRIIa, it is preferably coupled to the respective Fc receptor itself. This increases the antgenicity. The coupling can occur by chemical linkage or other suitable means.

This method preferably produces an immunogen with a high density of CDEs thereby presenting them in a different thus immunogenic environment. The initial immune response is directed against the targeted region (CDE) which produces antibodies that crossreact with the native structure to which they are coupled. These crossreacting antibodies mature towards higher affinity also recognizing the CDE in its natural environment.

The peptides of the invention and the CDEs may also be used in screening of molecular libraries for binding molecules (e.g. peptides, organic molecules, peptidometics etc.) or genetically encoded libraries (e.g phage display of antibody variable domains or other frameworks like lipocalines) to find specifically binding substances to FcγRIIb (or to FcγRIIa). The peptides may be used to screen libraries of molecules binding specifically to either FcγRIIa or FcγRIIb on human cells.

Similar peptides according to the invention can be extracted from the structure of other proteins, e.g. receptors, that are related to each other but which have different functions (e.g. human FcγRIIa-specific antibodies can be developed that do not recognize FcγRIIb, which may be incorporated in Diabodies or Triabodies, to promote ADCC which is mediated by FcγRIIa rather than by FcγRIIIb) or which occur in different alleles (e.g. FcγRIIa Arg/His-polymorphism at position 131, or FcγRIIIa Phe/Val-polymorphism at position 155).

Another use of the novel peptides of the invention is a direct use as inhibitors of promoters of immunological functions. The peptides according to the invention may be used directly for immunotherapies.

The above-described peptides of the invention can be produced by a novel method, wherein the method comprises:
  (a) providing a protein of interest,
  (b) identifying a CDE on that protein,
  (c) producing a peptide comprising the sequence of the CDE,
  (d) structurally stabilizing the peptide so that the CDE is present in its native conformation.

The peptide is structurally stabilized by circularisation, preferably by N- to C-terminal coupling, the formation of cysteine bridges, and/or bridging amino acid side chains forming a pseudopeptide. As stated above, the peptide is preferably generated using amino acids carrying glycosylation moieties which are present on the protein of interest. The method preferably comprises the additional step of conjugating the peptide to a carrier molecule which can be selected from any of the molecules mentioned above. Another aspect of the present invention is a peptide or polypeptide comprising a CDE, obtainable by the method of the invention.

In order to significantly raise the fraction of specifically binding antibodies, the invention provides the following method for generating specific binding substances capable of discriminating between an antigen of interest and closely related antigens, wherein the method comprises immunising an animal with a peptide or polypeptide according to the present invention or/and with a correctly folded portion of the antigen of interest, in particular a peptide derived from an Fc receptor such as FcγRIIb or FcγRIIa, and isolating the resulting antibodies, and optionally using the antibodies to generate recombinant immunomodulatory substances.

To produce antibodies that discriminate between an antigen A and an antigen B with high sequence identity to A, the differing amino acids are mapped to the structure of A or a respective structure model of A. Differing amino acids that are separated by several amino acids in the primary sequence may be in spatial proximity. In case that these differing amino acids are accessible from the solvent in the native structure these surface regions can be regarded as conformationally discriminating epitopes (CDE). Such epitopes can be artificially constructed by cyclic peptides or peptide analogues and are especially useful for the generation of antibodies that can discriminate between strongly related antigens.

In a variation of this method transgenic animals are used for immunization that are engineered to express the close homologue(s) and are later immunized with the target antigen. Animals that express the human FcγRIIb are immunized with human FcγRIIa or vice versa.

In a particularly preferred aspect, the present invention provides an FcγRIIb-binding antibody or fragment or derivative thereof, capable of specifically binding to FcγRIIb or to FcγRIIa in the natural environment of the Fc receptor. Such antibodies fragments or derivatives can discriminate between the closely related homologues of FcγRIIb and FcγRIIa in a natural environment, e.g in cell culture or in vivo.

In a preferred embodiment, the FcγRIIb- (or FcγRIIa-) binding antibody or fragment or derivative thereof not only binds specifically to FcγRIIb (or FcγRIIa) but also prevents the natural binding partners of FcγRIIb (or FcγRIIa), i.e. IgG antibodies, from binding.

In another preferred embodiment of the present invention, the specific anti-FcγRIIb (or anti-FcγRIIa) antibodies are non-blocking and recognize an epitope distinct from the Fc-receptor/Fc-fragment interaction site (e.g. an epitope of the N-terminal domain around the amino acids 28-31). In contrast to blocking antibodies these antibodies have the advantage that binding of the receptor to immune complexes is not impaired. The result is that the activation of the receptors by immune complexes remains intact and additional receptors can be recruited to enhance the activation.

It is thus possible to modulate the natural functions of these Fc receptors independent of IgG binding. For example, the antibody or fragment or derivative thereof may be chosen to be capable of crosslinking the Fc receptor. That way, the receptor can be activated. Preferably, the antibody or fragment or derivative thereof of the invention does not interfere with immune complex binding to FcγRIIb or FcγRIIa.

On the other hand, the antibody or fragment or derivative thereof may be chosen so that it inhibits the physiological function of human FcγRIIa or FcγRIIb.

The antibody or derivative or fragment of the invention preferably binds with higher affinity to FcγRIIb than to FcγRIIa. The antibody or fragment or derivative thereof binds FcγRIIb with at least 5 fold, preferably at least 10 fold, preferably at least 100 fold, more preferably at least 1,000 fold, more preferably at least 10,000 fold, more preferably at least 100,000 fold, more preferably at least $10^6$ fold, more preferably at least $10^7$ fold, more preferably at least $10^8$ fold, more preferably at least $10^9$ fold, more preferably $10^{10}$ fold, more preferably $10^{11}$ fold, more preferably $10^{12}$ fold higher affinity than FcγRIIa. Alternatively, the antibody or fragment or derivative binds FcγRIIa with at least 5 fold, preferably at least 10 fold, preferably at least 100 fold, more preferably at least 1,000 fold, more preferably at least 10,000 fold, more preferably at least 100,000 fold, more preferably at least $10^6$ fold, more preferably at least $10^7$ fold, more preferably at least $10^8$ fold, more preferably at least $10^9$ fold, more preferably $10^{10}$ fold, more preferably $10^{11}$ fold, more preferably $10^{12}$ fold higher affinity than FcγRIIb. 5, 10, 100, 1000 or even more than 1,000,000 fold tighter binding to the specific Fc-receptor is necessary to overcome the much higher expression level of FcγRIIa on platelets over FcγRIIb.

The antibody or fragment or derivative thereof can occur in a monomeric or multimeric state.

The antibody or fragment or derivative thereof may be capable of binding Fc receptor molecules with or without cross-linking them on the cell surface. Preferably, the antibody or fragment or derivative thereof is multimeric in order to cross-link FcγRIIa or FcγRIIb. Alternatively, the antibody or fragment or derivative thereof is monomeric and able to block IgG binding to human FcγRIIb, but preferably not able to cross-link FcγRIIb.

The antibody or fragment or derivative thereof of the invention may also be modified in the Fc-fragment by the modification of the glycosylation and/or mutagenesis to enhance the binding towards subsets of the Fc-receptors.

The antibody or fragment or derivative thereof of the invention is preferably able to bind to a CDE or/and peptide as described above, in particular those comprising one or more of the amino acids of human FcγRIIb according to FIG. 1 and SEQ ID NO: 2, selected from: Gln12, Arg27, Thr29, His30, Val104, Lys127, Ser132, Asn135, Tyr160, and Ala171, or the corresponding amino acids of FcγRIIa according to SEQ ID NO: 1. More preferably, the substance binds to an epitope comprising amino acids 27 to 30, and/or 127 to 135, and/or 160 to 171 of the amino acid sequence of FcγRIIb (FIG. 1, SEQ ID NO: 2) or the corresponding epitopes of FcγRIIa.

In a similar way human FcγRIIIa-specific antibodies can be developed that do not recognize FcγRIIIb, which may be incorporated in Diabodies or Triabodies, to promote ADCC which is mediated by FcγRIIIa rather than by FcγRIIIb.

The antibody or fragment or derivative thereof can be any natural, artificial or recombinantly produced substance carrying a region which can bind to the above-mentioned epitopes of FcγRIIb. Preferably, this region contains the complementarity determining regions (CDRs) of the antibody which bind specifically to FcγRIIb. More preferably, the CDRs comprise the sequences as depicted in FIGS. 5 and 6.

The described CDRs maybe the basis for variations to further improve their specificity or designing new specific or pan-antibodies (or binding molecules) for other selected Fc-Receptors or receptor groups. Methods are known that include random or site directed mutagenesis, screening for related sequences and knowledge- or structure-based design.

Preferably, the antibody or fragment or derivative thereof comprises one or both of the variable light and variable heavy regions according to SEQ ID Nos: 5 and 7, and/or the variable light and variable heavy regions according to SEQ ID Nos: 9 and 11. Most preferably, the antibody is CE5 or GB3.

Monoclonal antibodies are preferred. Preferably, it is an antibody or fragment or derivative thereof having an IgG, IgE, IgM or IgA isotype. Preferably, the antibody is human or humanized, but may also be of other origin, such as animal origin, in particular of mouse or camel origin. The antibody may be in various forms, such as a single chain antibody, bi- or tri-functional or multi-functional antibody, Fab- of Fab$_2$-fragment or as entire antibody in which the Fc-fragment has a modified affinity towards Fc receptors or complement. It may also be a Fab fragment, a F(ab)$_2$ fragment, or a Fv fragment, or an scv fragment.

The antibody or fragment or derivative thereof may also be a recombinantly produced polypeptide or polypeptide analogue which has a specific binding region comprising the sequence of the CDRs or a similar sequence related to more than 50%, preferably more than 70%, preferably more than 90%, preferably more than 95% to the provided sequences. These sequences may also be the starting point for the design of inhibitors of Fc-receptors. Therefore, also peptidomimetica are part of the invention that use or mimic sequence motives of the provided CDRs.

In another preferred embodiment, the antibody or fragment or derivative thereof is an anticaline or lipocaline-variant or another antibody surrogate.

The obtained antibody or fragment or derivative thereof can be coupled to an effector molecule such as an antigen of interest, antibodies, antibody fragments, marker molecules, cytotoxic substances, sterically bulky blocking substances and linker molecules and linker substances.

Another aspect of the invention are nucleic acids, vectors and host cells containing nucleic acids encoding the peptides and/or the antibodies or fragments or derivatives thereof, of the present invention as described above.

From the antibody or fragment or derivative thereof according to the invention, a nucleic acid sequence encoding this protein can be derived. Preferably, that sequence encodes the variable regions, preferably the CDRs binding to the above mentioned epitopes of FcγRIIb. Most preferably, the nucleic acid sequence encodes the CDRs according to one or more of the sequences according to FIGS. 5 and 6. Preferably, the nucleic acid encodes the sequence of monoclonal antibodies CE5 or GB3.

The nucleic acid sequence may be inserted into a vector for the expression of the protein according to FIGS. 5 and 6, which vector is also an aspect of the present invention. The vector preferably comprises a promoter under the control of which the above nucleic acid sequences are placed. The vector can be prokaryotic or an eukaryotic expression vector, where the recombinant nucleic acid is either expressed alone or in fusion to other peptides or proteins or a vector suitable for DNA-vaccination.

The invention also provides a host cell transfected with the vector mentioned above. The host cell can be any cell, a prokaryotic cell or a eukaryotic cell.

The present invention further provides a pharmaceutical composition useful for the treatment of diseases associated with Fc receptor mediated signaling, comprising an effective amount of the antibody or fragment or derivative thereof according to the invention, and pharmaceutically acceptable carrier substances.

The present invention further provides a diagnostic kit for the detection of autoimmune diseases and/or cancer, comprising an antibody or fragment or derivative thereof according to the invention and/or the recombinant peptide or polypeptide according to the invention which comprises or represents one of the epitopes as described herein, and optionally marker reagents, carrier reagents and/or suitable receptacles.

Figure 3:
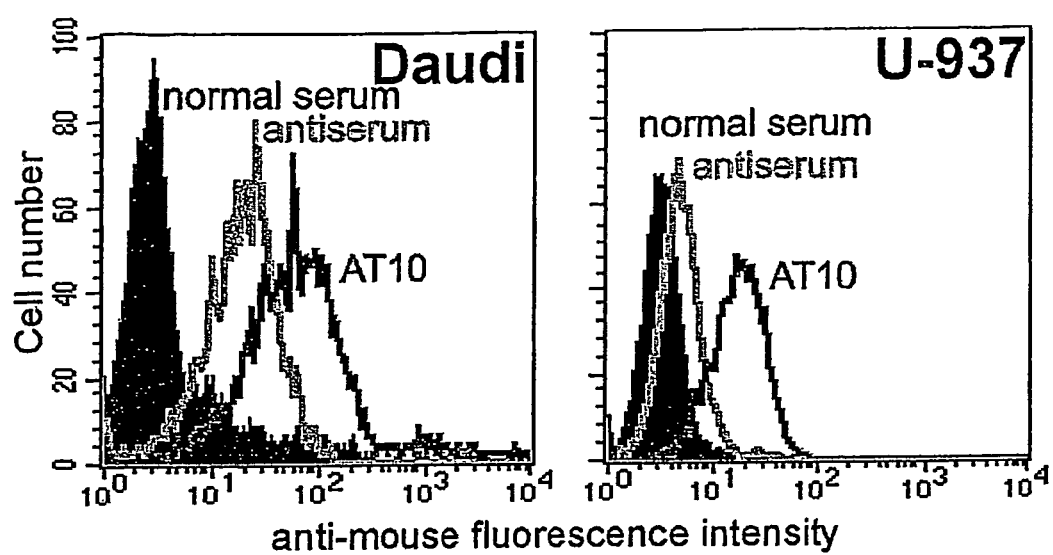
Figure 4:
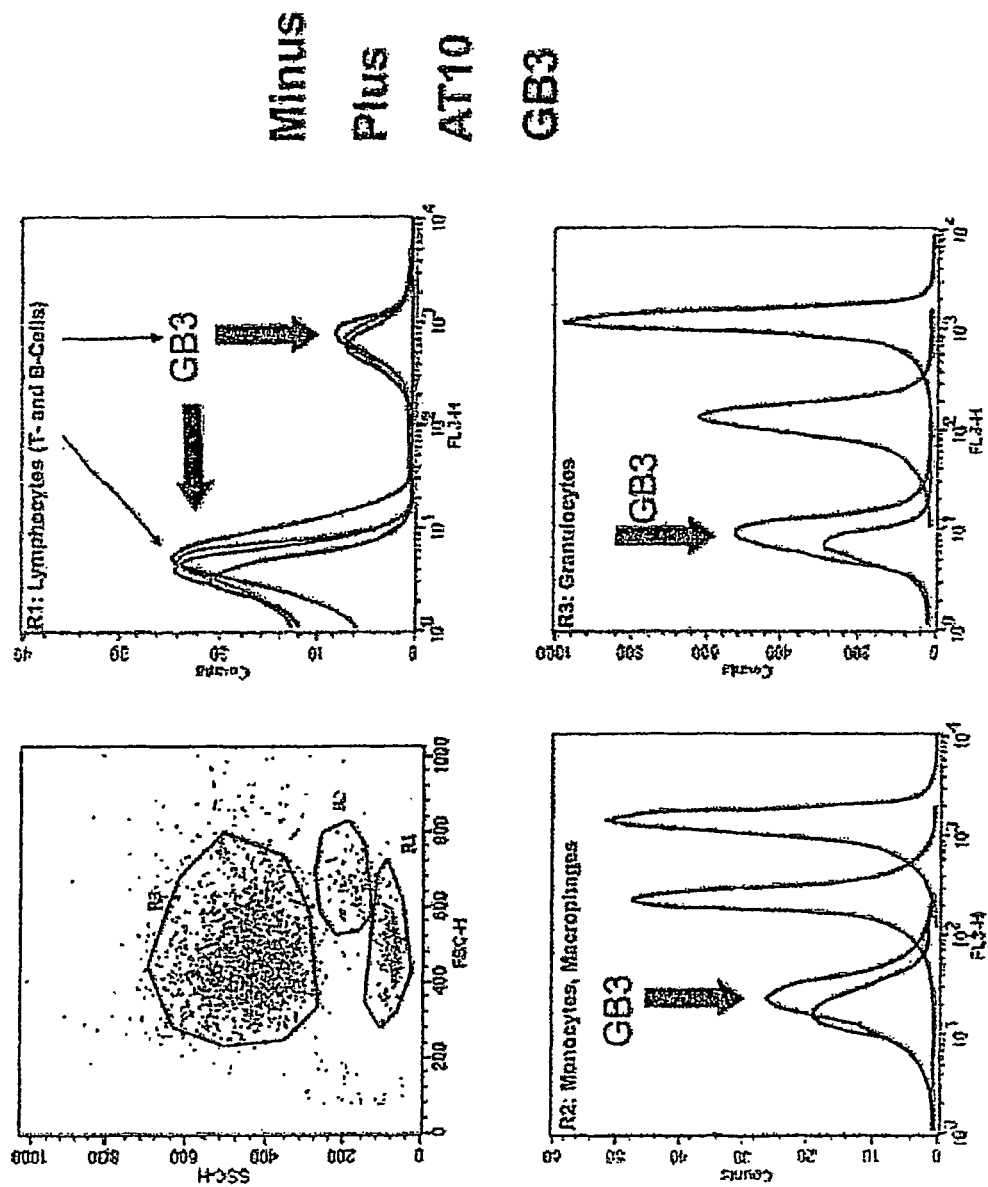

Immunization with unglycosylated correctly folded Fc-receptors, e.g. derived from *E. coli*, and decorated with the described epitopes surprisingly leads to antibodies that specifically recognize natural Fc-receptors expressed on blood cells and in cell culture (FIG. 3 and FIG. 4).

Another aspect of the present invention is a method of producing antibodies characterized by the ability to specifically bind to FcγRIIb, wherein the method comprises:
  (a) Providing the correctly folded FcγRIIb molecule or portion thereof as an immunogen, comprising at least a part of the extracellular domain (conformational epitopes), their conjugation, or conjugation with other carrier molecules (e.g. KLH, BSA).
  (b) Immunizing a mammal with the immunogen of (a) and producing antibodies according to known methods,
  (c) Isolating the resulting antibodies or the cells producing these antibodies.

The antibodies are preferably monoclonal antibodies.

The CDRs may be grafted to other immunoglobulin classes (e.g. IgM, IgE, IgG1-IgG4) or other scaffolds (e.g. lipocaline-variants, camel antibodies), or mutated or derivatised molecules (e.g. engineered antibodies containing a modified Fc-fragment).

The above described method may be used to produce vehicles for the immunization of animals and results in an anti-serum of increased specificity towards FcγRIIb, which after fusion of isolated B-cells with myeloma cells results in hybridoma cells with an increased fraction producing antibodies specific for FcγRIIb.

The antibody or fragment or derivative thereof according to the present invention is useful for the production of a medicament for the treatment and/or diagnosis of conditions involving the immune system. Preferably, these conditions are autoimmune diseases or cancer.

The diseases that can be treated with a medicament of the invention include, but are not limited to rheumatoid arthritis, psoriatic arthritis, ankylosing spondylitis, Rieter's syndrome, psoriasis, multiple sclerosis, lupus erythematosus.

Autoimmune diseases which can be diagnosed or treated using the substances of the present invention include, but are not limited to systemic lupus erythematosus, rheumatoid arthritis, Multiple Sclerosis, idiopathic thrombocytopenic purpura and host-versus-graft disease.

Surprisingly, it has been found by the present inventors that it is possible to enhance certain immunological processes by using the FcγRIIb-binding substances in vivo. In particular, it is possible to use those substances of the invention to specifically block the signaling of FcγRIIb on cells and thereby increasing the immune response of the individual. This may be used to increase ADCC against tumor cells. In practice the FcγRIIb-binding substance is given as adjuvant with a therapeutic antibody. The inhibitory signal transmitted by antigens (e.g. tumor cells) opsonized with the therapeutic antibody to activated macrophages or B-cells is blocked and the host immune system will be more effective in combating the targeted antigen. This can either be in a direct way by labeling tumor cells that express FcγRIIb (e.g. B cell lymphoma) or by using this FcγRIIb-binding substance as adjuvant in all approaches which use known therapeutic antibodies and therefore depend on the ADCC of the host.

The known therapeutic antibodies include but are not limited to Herceptin®, Rituxan®, IC14, PANOREX™, IMC-225, VITAXIN™, Campath 1H/LDP-03, LYMPHOCIDE™ and ZEVLIN™. They can also include antibodies binding to the following cancer antigens: MAGE-1, MAGE-3, BAGE, GAGE-1, GAGE-2, N-acetylglucosaminyltransferase, p15, beta-catenin, MUM-1, CDK4, HER-2/neu, human papillomavirus E6, human papillomavirus E7 and MUC-1.

In certain lymphomas B-cells or Mast-cells are transformed. The antibody or fragment or derivative thereof is able to cross link FcγRIIb on the surface of these cells, which labels these cells for elimination but additionally an inhibitory and pro apoptotic signal is transmitted to these cells. This effect is an improvement of previous therapeutic antibody approaches, which completely depend on the ADCC of the host (e.g. Rituxan).

The same antibody that crosslinks or blocks Fc-receptors may be used for the treatment of host-versus-graft disease or amyloid associated diseases.

The same FcγRIIb blocking and/or cross linking constructs maybe used to inhibit mast cells for the treatment of allergies.

The antibody or fragment or derivative thereof maybe coupled to IgE (e.g. by transferring the CDRs shown in FIG. 5 or 6 to an IgE molecule). In this case the IgE is bound by the Mast-cell expressed FcεRI and the FcγRIIb specific CDRs cross link the ITAM of FcεRI with the ITIM of the FcγRIIb. Again an inhibitory and/or apoptotic signal is transmitted to Mast-cells, which is useful in the therapy of allergies.

The antibody or fragment or derivative thereof (e.g derivatives of the sequences depicted in FIGS. 5 and 6) maybe used for the treatment of autoimmune diseases.

Such substances inhibit B-cells, dendritc cells and activated ganulocytes (e.g Macrophages) which leads to a reduced production of immune stimulatory mediators and to a reduction in antibody production as well as antigen presentation (e.g. on Dendritic Cells and Macrophages leading to a decrease in T-cell recruitment). Taken together the feed back loop of antibody production and restimulation of the immune system is inhibited.

Preferably the anti-FcγRIIb or FcγRIIa does not interfere with Fc-fragment binding of the receptor. In this way the normal function of the Fc-receptor is in contrast to blocking antibodies maintained and enhances the activation of the cell by the additional recruitment of further receptors.

On the other hand specific anti-FcγRIIa antibodies or fragments thereof maybe used in diabodies to direct an antigen towards this receptor or fragments of these antibodies maybe used to inhibit the uptake of immune complexes for example for the treatment of ITP.

The CDRs can be used alone or in combination for the production of specific inhibitors of the FcγRIIa/IgG interaction or the FcγRIIb/IgG interaction. For the generation of such inhibitors, derivatives or peptidomimetics as well as non-natural amino acids may be used.

The inhibitors may in turn be used to generate crystal structures or for structure based design or as subject for evolutionary methods. A further use is the generation of modified sequences from that depicted in FIG. 5 or 6 by evolutionary methods (e.g. random or site directed mutagenesis or structure based design).

In particular, the inhibitors of Fc receptors may be used to reduce or enhance the specificity of the above for the selected Fc-receptors. To this end, modifications can be carried out in the CDRs of the specific antibodies, in particular of GB3 and CE5, in order to enhance or lower their specificity to FcγRIIb.

The peptides and polypeptides and substances of the invention, in particular the antibody or fragment or derivative thereof are useful for the production of a medicament for the treatment and/or diagnosis of conditions involving the immune system, in particular autoimmune diseases, preferably those selected from Systemic Lupus Erythematosus, Rheumatoid Arthritis, Immune Thrombocytopenic Purpura or Multiple Sclerosis. Further uses of the peptides and antibodies or fragments or derivatives thereof of the invention are in the diagnosis and/or treatment of cancer and/or allergies. The mAbs CE5 or GB3 or derivatives or fragments thereof are particularly useful for the treatment of autoimmune diseases, Multiple sclerosis, Systemic Lupus Erythematosus, Idiopathic Thrombocytopenic Purpura, Rheumatoid Arthritis, and cancer, in particular lymphomas or leukemias.

The mAbs CE5 or GB3 or derivatives or fragments thereof can also be used for the treatment of cancer in combination with other therapeutics preferably biotherapeutics (e.g. antibodies).

The antibody or derivatives or fragments thereof generated according to the present invention can be used for the treatment and/or diagnosis of cancer, preferably in combination with other therapeutics, preferably biotherapeutics (e.g. further antibodies). The antibody or fragment or derivative thereof is then preferably used as an adjuvant.

Further uses of the antibody or fragment or derivative thereof of the invention include the use for the production of pharmaceutical and/or diagnostic compositions for the treatment of host-versus-graft disease, for the treatment of amyloid linked diseases or to increase the effect of vaccination or for the treatment of diseases associated activated dendritc cells and/or macrophages.

It is also possible to use an antibody or fragment or derivative thereof which comprises specific anti-FcγRIIa fragments in bi-specific antibodies to direct antigens towards transport by thrombocytes and/or uptake by the liver and spleen phagocytosis system. Preferably, the antibody or fragment or derivative thereof is a specific anti-FcγRIIa antibody or fragment thereof for the treatment of ITP.

DESCRIPTION OF FIGURES AND SEQUENCE LISTING

FIG. 1: Sequence alignment of the extracellular domains of the human FcγRIIb and FcγRIIa. Differing amino acids are boxed.

FIG. 2: Structure of FcγRIIb in ribbon representation. The unique residues are shown in ball-and-stick and potential glycosylation sites are indicated as larger spheres. Arrows point to possible extractable substructures (epitopes 1 and 2) that may be artificially generated for the improvement of immunization protocols towards specific FcγRIIb-antisera and subsequently for the production of isoform specific monoclonal antibodies.

FIG. 3: Left diagram: Histogram of a FACS measurement of Raji cells (FcγRIIb-positive and FcγRIIa-negative) using the preimmune serum of the mouse (minus), the obtained antiserum after the immunization procedure (antiserum) and the pan-FcγRII-mAb AT10 (Greenman et al., 1991). Right diagram: Fluorescence label on U-937 cells. (FcγRIIa-positive and FcγRIIb negative). The antiserum reacts only marginally with the cells indicating the presence of specific antibodies.

FIG. 4: FACS analysis of human blood incubated either with normal serum (negative control), antiserum of a mouse immunized with FcγRIIb-CDE[126-137], mAb AT10 or the specific monoclonal antibody GB3 generated by using this invention. a): Dotblot analysis of the blood sample in terms of cell size (FSC-H) and granularity (SSC-H). The observed regions R1, R2 R3 contain lymphocytes (B and T cells), monocytes and granulocytes respectively. b) Fluorescence intensity of the cells found in region R1 representing lymphocytes. The pan-FcγRIIb mAb AT10, the mAb GB3 and the antiserum stain the FcγRIIb-positive B-cells while the FcγRII-negative T cells are not recognized. c) Fluorescence intensity of the cells found in region R2 representing monocytes/macrophages. In contrast to the positive controls mAb AT10 and the antiserum the mAb GB3 does not recognize the FcγRIIa-positive monocytes. d) Fluorescence intensity of the cells found in region R3 representing granulocytes. In contrast to the positive controls mAb AT10 and the antiserum the mAb GB3 does not recognize the FcγRIIa-positive granulocytes.

FIG. 5: The variable regions of the cloned antibody GB3. The boxed regions represent the CDRs while the underlined termini may vary due to cloning artifacts introduced by the primer. a) Variable region of the light chain; b) Variable region of the heavy chain.

FIG. 6: The variable regions of the cloned antibody CE5. The boxed regions represent the CDRs while the underlined termini may vary due to cloning artifacts introduced by the primer. a) Variable region of the light chain; b) Variable region of the heavy chain.

FIG. 7: The glycopeptide CDE[126-137] used for immunization and generation of FcγRIIb-specific antibodies.

Figure 8:
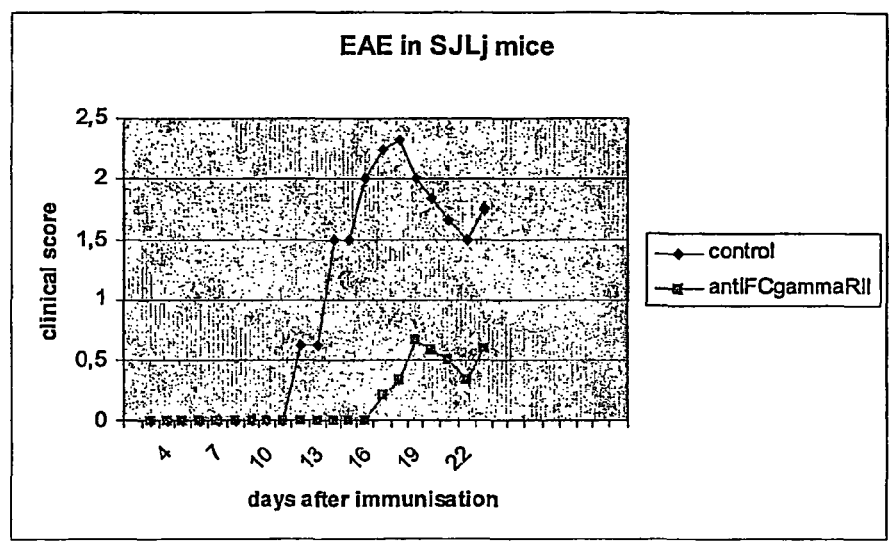

FIG. 8: Immunisation of SJL mice with a specific anti-mouse FcγRII antibody. SJLj were immunized with 200 μg MOG an day 0. Treatment with antiFcγRII antibody (dosis of 50 μg/week) started at day 5. The clinical score was monitored daily and is given as the average of the 8 mice per group.

SEQ ID NO: 1 amino acid sequence of FcγRIIa (as in FIG. 1)

SEQ ID NO: 2 amino acid sequence of FcγRIIb (as in FIG. 1)

SEQ ID NO: 3 sequence of the glycopeptide CDE [126-137]

SEQ ID NO: 4 nucleic acid sequence of the variable light region of mAb GB3

SEQ ID NO: 5 corresponding amino acid sequence of the variable light region of mAb GB3

SEQ ID NO: 6 nucleic acid sequence of the variable heavy region of mAb GB3

SEQ ID NO: 7 corresponding amino acid sequence of the variable heavy region of mAb GB3

SEQ ID NO: 8 nucleic acid sequence of the variable light region of mAb CE5

SEQ ID NO: 9 corresponding amino acid sequence of the variable light region of mAb CE5

SEQ ID NO: 10 nucleic acid sequence of the variable heavy region of mAb CE5

SEQ ID NO: 11 corresponding amino acid sequence of the variable heavy region of mAb CE5

EXAMPLES

Example 1

Synthesis of the Cyclo-[N-β-(2-acetylamino-deoxy-2-β-glucopyranosyl)-Asn$^{138}$, Gly$^{141}$]-(129-141)-FcγRIIb2, CDE[126-137]

Standard amino acid derivatives were from Alexis (Läufelfingen, Switzerland), Fluorenylmethoxycarbonyl-derivative (Fmoc) of Asn(N-β-3,4,6-tri-O-acetyl-2-acetylamino-deoxy-2-β-glucopyranosyl)-OH from Merck-Novabiochem (Darmstadt, Germany), and the preloaded chlorotrityl resin from Pepchem (Tübingen, Germany). Reagents and solvents were of the highest quality commercially available and were used without further purification. Analytical reversed-phase HPLC was performed on Waters equipment (Eschborn, Germany) with a Symmetry $C_{18}$ column (5 μm, 3.9×150 mm, Waters) by linear gradient elution: (1) 0-100% A in 15 min, or (2) 0-30% A in 20 min, up to 50% A in 5 min and to 100% A in further 5 min, (flow rate of 1.5 ml/min and UV detection at 210 nm). The binary elution system was (A) acetonitrile/2% $H_3PO_4$ (90:10) and (B) acetonitrile/2% $H_3PO_4$ (5:95). Preparative reversed-phase HPLC was carried out on Abimed equipment (Langenfeld, Germany) using Nucleosil $C_{18}$ PPN (5 μm, 100 Å, 10×250 mm, Macherey-Nagel, Düren, Germany) and a gradient of 0.08% trifluoroacetic acid (TFA) in acetonitrile (A) and 0.1% TFA in water (B) at a flow rate of 10 ml/min: 2% A for 7 min, up to 40% A in 50 min and to 70% A in further 5 min. ESI-MS spectra were recorded on a Perkin-Elmer SCIEX API 165 triple quadrupole spectrometer. LC-MS was carried out with a Nucleosil $C_{18}$ column (5 μm, 100 Å, 1×250 mm, Macherey-Nagel) using linear gradients of 0.1% TFA in water and 0.08% TFA in acetonitrile (flow rate: 30 μl/min; detection at 210 nm).

a) Solid-Phase Peptide Synthesis.

The linear peptide precursor was synthesized manually on Fmoc-Gly-chlorotrityl resin (232 mg, 0.13 mmol) following standard procedures of Fmoc/tert-butyl (tBu) chemistry. The Fmoc group was cleaved in each step with two successive treatments (3 and 20 min) with 20% piperidine in N-methyl pyrrolidone (NMP). For Fmoc-Ser(tBu)-OH and Fmoc-Phe-OH double couplings (2×1 h) with Fmoc-amino acid/2-(1H-benzotriazol-1-yl)-1,1,3,3-tetramethyluronium hexafluorophosphate (HBTU)/N-hydroxybenzotriazole (HOBt)/N,N-diisopropylethylamine (DIEA) (4:4:4:8 eq) in NMP were applied, whereas the glycosylated Asn derivative was introduced by single coupling using Fmoc-aminoacid/(1H-benzotriazol-1-yloxy)-tripyrrolidinophosphonium hexafluorophosphate (PyBOP)/HOBt/DIEA (2:2:2:5 eq) in NMP. The reaction was complete after 5 h, as confirmed by the Kaiser test. A capping step with acetic anhydride/DIEA (1:1, 3 eq) for 10 min was performed prior to chain elongation. For acylation with the remaining amino acid derivatives (Arg was introduced as Arg-2,2,4,6,7-pentamethyl-dihydrobenzofurane-5-sulfonyl [Pbf] derivative) again double couplings (2×1.5 h) were used with Fmoc-amino acid/HBTU/HOBt/DIEA (6:6:6:12 eq) in NMP.

b) Cleavage of the Side-Chain-Protected Peptide.

The side-chain-protected linear peptide was cleaved from the resin by treating the peptide-resin with 5 ml of 1% TFA in dichloromethane (DCM) for 3 min. The filtrate was analyzed by thin layer chromatography (TLC) ($CH_3Cl/MeOH/H_2O$, 8:3:1) prior to addition of 1 ml of 10% pyridine in methanol. The TFA treatment was repeated until the TLC control on the filtrate was negative (overall four treatments). Finally, the resin was washed with DCM and trifluoroethanol to improve the peptide recovery. The peptide-containing filtrates and the final washes were combined and concentrated to a small volume. The residue was diluted with MeOH, and the product was precipitated with ice-cold water. The crude product was collected by filtration (270 mg, 80% yield) and characterized by analytical HPLC (gradient 1) and ESI-MS. A major peak ($t_R$ 9.5 min; ESI-MS: m/z=2520 [M+H]$^+$; $M_r$=2519.0 calcd for $C_{120}H_{188}N_{20}O_{36}S$) and a minor peak ($t_R$ 9.3 min; ESI-MS: m/z=2478 [M−42+H]$^+$) at the ratio of 75:20 were found to correspond to the expected product and to a side product, respectively. The mass difference was attributed to the loss of one acetyl protecting group from Asn(Ac$_3$AcNH-β-Glc).

c) Cyclization.

Backbone cyclization was accomplished at a peptide concentration of 0.9 mM in N,N-dimethylformamide (DMF), in the presence of PyBOP/HOBt/DIEA (1.5:1.5:3.5 eq). The base was added in portions over 1 h. The conversion of the linear peptide to the cyclic form was monitored by analytical HPLC, and was completed after 2.5 h. The reaction mixture was taken to dryness, and the residue was triturated and washed with ice-cold diethyl ether to remove traces of DMF prior to the TFA cleavage.

d) Cleavage of the Side-Chain Protecting Groups.

The acid-labile side-chain protecting groups were removed by dissolving the cyclic peptide in 10 ml the ice-cold TFA/triisopropylsilane (TISH)/$H_2O$ (90:5:5). After 2 h shaking, the TFA was removed under reduced pressure, the oily residue was diluted with a small amount of MeOH and the crude product precipitated with ice-cold diethyl ether. The precipitate was collected by centrifugation, washed several times with ice-cold ether and, finally, lyophilized from water. The crude glycopeptide which in addition to the triacetylated form, according to LC-MS was contaminated by the di- and mono-acetyl derivatives, was suspended in MeOH and treated in portions with NaOMe over 30 min until an apparent pH of >10 was reached. The reaction was monitored by HPLC, and after 3.5 h it was quenched by addition of glacial acetic acid until pH<5. The mixture was taken to dryness, and the solid was suspended in MeOH and reprecipitated with ice-cold diethyl ether. The precipitate was collected by filtration and lyophilized from water. The crude product was purified by preparative HPLC and the cyclic glycopeptide was isolated as lyophilized material; yield: 20% yield (based on the starting resin loading of 0.13 mmol); HPLC: >95% ($t_R$ 7.37 min with gradient 2); ESI-MS: m/z=1642.8 [M+H]$^+$; M=1641.8 Da calculated for $C_{71}H_{108}N_{20}O_{25}$.

Coupling of the CDE[126-137] to FcγRIIb Yielding FcγRIIb-CDE[126-137]

100 μl human soluble FcγRIIb (10.6 mg/ml) were added to 1490 μl 50 mM borate pH10 and 410 μl of the glycopeptide CDE[126-137] (2 mg/ml) and stirred gently at room temperature. 100 μl of a 0.3% glutaraldehyde solution were slowly added and the whole mixture stirred for another two hours at RT before 100 μl 1M glycine was added. The resulting FcγRIIb-CDE[126-137] was stirred for another 30 min and then dialyzed against PBS and concentrated.

Example 2

Immunization with FcγRIIb-CDE[126-137]

A female six weeks old C57Bl/6 mouse was immunized intraperitoneally every two weeks with an emulsion of 50 μg FcγRIIb-CDE[126-137] in 100 μl Complete Freunds Adjuvant (CFA, Sigma/Deisenhofen, Germany) for three times. Three weeks after the last immunization the mouse was boosted with 50 μg of the FcγRIIb-CDE[126-137]: Three days later the spleen was removed from the animal and the fusion of the extracted cells with myeloma cells was performed according to Bazin, and Lemieux, 1989.

Example 3

Screening of the Hybridoma for FcγRIIb-CDE[126-137]-Specificity

Clones that were able to grow in the presence of hypoxanthine, aminopterin, and thymidine were isolated and their supernatant tested in ELISA assays where FcγRIIb-CDE[126-137] was precoated on microtitre plate with 120 ng sFcγRIIa/b per well (in 100 μl PBS, 20° C., 12 h). The plate was washed and incubated with PBS/T (PBS/0.2% Tween 20, 30 min). 100 μl of the respective hybridoma were added to the well (100 μl, 90 min). The plate was washed three times with blocking buffer before 100 μl of a peroxidase labeled goat-anti mouse IgG+IgM antibody (Dianova, Hamburg/Germany) diluted in PBS/T was added. After incubating for 90 min and subsequent washing with PBS/T, 100 μl of substrate buffer (0.2 M citrate/phosphate buffer pH 5.2, 4 mg/ml o-phenylenediamine, 0.024% (v/v) hydrogenperoxide) were applied to the wells. The reaction was stopped by adding 50 μl 8 N sulfuric acid and the absorbance at 490 nm was measured in an ELISA reader.

Clones that were positive in this assay were tested by flow cytometry (FACS) using $10^5$ Raji cells per sample (ATCC CCL-86) which strongly express human FcγRIIb. After incubation with 100 μl hybridoma supernatant for 30 min on ice the cells were washed with 1 ml RPMI/10% FCS and precipitated by centrifugation (400×g, 4° C., 5 min). 100 μl FITC labeled goat anti human antibody (Dianova, Hamburg/Germany) were added. After incubation for 30 min on ice the cells were washed (RPMI/10% FCS) and subjected to flow cytometry (FACSort, Becton Dickinson, Heidelberg/Germany). The median value of the fluorescence for 5,000 counted cells was determined for each sample. Hybridoma supernatants that were positive in this assay were subjected in a similar assay using U-937 cells (ATCC CRL-1593.2) which strongly express FcγRIIa to determine FcγRIIb-specificity of the hybridoma. As positive control for both cell lines the pan-FcγRII-mAb AT10 (Greenman et al., 1991) was used.

Example 4

Immunisation of SJL Mice with a Specific Anti-Mouse FcγRII Antibody

SJL-Mice were immunized with 200 μg MOG to induce Experimental Autoimmune Encephalomyelitis (EAE) an established animal model of Multiple Sclerosis. Prophylactic as well as therapeutic (data not shown) treatment of 8 mice per group with a specific anti-mouse FcγRII antibody (50 μg/week) significantly reduces the symptoms (clinical score) of the disease (0=healthy, 1=light paralysis, 2=medium paralysis, 3=strong paralysis, 4=complete paralysis, 5=death). The results are shown in FIG. 8.

REFERENCES

Amigorena, S., Bonnerot, C., Drake, J. R., Choquet, D., Hunziker, W., Guillet, J. G., Webster, P., Sautes, C., Mellman, I., Fridman, W. H. (1992), Cytoplasmic domain heterogeneity and functions of IgG Fc receptors in B lymphocytes, Science 256, 1808-1812.

Bazin, R. and Lemieux, R. (1989), Increased proportion of B cell hybridomas secreting monoclonal antibodies of desired specificity in cultures containing macrophage-derived hybridoma growth factor (IL-6). J. Immunol. Methods 116, 245-249.

Ceuppens, J. L., Baroja, M. L., van Vaeck, F., Anderson, C. L. (1988), Defect in the membrane expression of high affinity 72 kD Fc© receptors on phagocytic cells in four healthy subjects, J. Clin. Invest. 82, 571-578.

Clynes, R. A., Towers, T. L., Presta, L. G., Ravetch, J. V. (2000), Inhibitory Rc receptors modulate in vivo cytotoxicity against tumour targets. Nature Medicine 6, No. 4, 443-446.

Engelhardt, W., Geerds, C., Frey, J. (1990), Distribution, inducibility and biological function of the cloned and expressed human© Fc receptor II, Eur. J. Immunol. 20, 1367-1377.

Fridman, W. H., Bonnerot, C., Daeron, M., Amigorena, S., Teillaud, J.-L., Sautès, C. (1992), Structural bases of FcγR functions, Immunol. Rev. 125, 49-76.

Fridman, W. H., Teillaud, J.-L., Bouchard, C., Teillaud, C., Astier, A., Tartour, E., Galon, J., Mathiot, C., Sautès, C. (1993), Soluble Fc© receptors, J. Leukocyte Biol. 54, 504-512.

Greenman, J., Tutt, A. L., George, A. J., Pulford, K. A., Stevenson, G. T., Glennie, M. J. (1991), Characterization of a new monoclonal anti-Fc gamma RII antibody, AT10, and its incorporation into a bispecific F(ab')2 derivative for recruitment of cytotoxic effectors. Mol. Immunol. 28, 1243-1254.

Homsy, J., Meyer, M., Tateno, M., Clarkson, S., Levy, J. A. (1989), The Fc and not CD4 receptor mediates antibody enhancement of HIV infection in human cells, Science 244, 1357-1360.

Isakov N. (1997), ITIMs and ITAMs. The Yin and Yang of antigen and Fc receptor-linked signaling machinery. Immunol Res. 16, 85-100.

Littaua, R., Kurane, I. and Ennis, F. A. (1990), Human IgG FcγR II mediates antibody-dependent enhancement of dengue virus infection, J. Immunol. 144, 3183-3186.

Metzger, H. (1992A), Transmembrane signaling: The joy of aggregation, J. Immunol. 149, 1477-1487.

Metzger, H. (1992B), The receptor with high affinity for IgE, Immunol. Rev. 125, 37-48.

Poo, H., Kraus, J. C., Mayo-Bond, L., Todd, R. F., Petty, H. R. (1995), Interaction of FcγRIIIB with complement receptor type 3 in fibroblast transfectants: evidence from lateral diffusion and resonance energy transfer studies, J. Mol. Biol. 247, 597-603.

Ravanel, K., Castelle, C., Defrance, T., Wild, T. F., Charron, D., Lotteau, V., Rabourdincombe, C. (1997), Measles virus nucleocapsid protein binds to FcγRII and inhibits human B cell antibody production. J. Exp. Med. 186, 269-278.

Ravetch, J. V. and Bolland, S. (2001), IgG Fc Receptors. Annu. Rev. Immunol. 19, 275-290.

Sondermann, P., Jacob, U., Kutscher, C., Frey J. (1999A), Characterization and crystallization of soluble human Fcγ receptor II (CD32) isoforms produced in insect cells. Biochemistry. 38, 8469-8477.

Sondermann, P. and Jacob, U. (1999B), Human Fcγ receptor IIb expressed in *E. coli* reveals IgG binding capability. Biol Chem. 380, 717-721.

Sondermann P, Huber R, Oosthuizen V, Jacob U. (2000), The 3.2 Å crystal structure of the human IgG1 Fc fragment-FcγRIII complex Nature 406, 267-273.

Sondermann P, Kaiser J, Jacob U. (2001), Molecular basis for immune complex recognition: a comparison of Fc-receptor structures. J Mol Biol. 309, 737-749.

van de Winkel, J. G. J. and Capel, P. J. A. (1993), Human IgG Fc receptor heterogeneity: Molecular aspects and clinical implications, Immunol. Today 14, 215-221.

Yang, Z., Delgado, R., Xu, L., Todd, R. F., Nabel, E. G., Sanchez, A., Nabel, G. J. (1998), Distinct cellular interactions of secreted and transmembrane Ebola virus glycoproteins, Science 279, 983-984.

Zhou, M.-J., Todd, R. F., van de Winkel, J. G. J., Petty, H. R. (1993), Cocapping of the leukoadhesin molecules complement receptor type 3 and lymphocyte function-associated antigen-1 with FcγRIII on human neutrophils. Possible role of lectin-like interactions, J. Immunol. 150, 3030-3041.

---

The invention claimed is:

1. An antibody that specifically binds to the amino acid sequence of FcγRIIb according to SEQ ID NO: 2, wherein the antibody comprises the variable light chain region of antibody according to SEQ ID NO: 5.

2. An antibody that specifically binds to the amino acid sequence of FcγRIIb according to SEQ ID NO: 2, wherein the antibody comprises the variable heavy chain region of antibody according to SEQ ID NO: 7.

3. The antibody of claim 1, wherein the antibody further comprises the variable heavy region of antibody according to SEQ ID NO: 7.

* * * * *